(12) United States Patent
Ferguson

(10) Patent No.: US 6,422,090 B1
(45) Date of Patent: Jul. 23, 2002

(54) APPARATUS FOR A THERMODYNAMIC MATERIAL TESTING SYSTEM THAT PRODUCES VERY LARGE STRAINS IN CRYSTALLINE METALLIC SPECIMENS AND ACCOMPANYING METHODS FOR USE THEREIN

(75) Inventor: Hugo S. Ferguson, Tarpon Springs, FL (US)

(73) Assignee: Dynamic Systems Inc., Poestenkill, NY (US)

( * ) Notice: Subject to any disclaimer, the term of this patent is extended or adjusted under 35 U.S.C. 154(b) by 0 days.

(21) Appl. No.: 09/543,021

(22) Filed: Apr. 4, 2000

Related U.S. Application Data

(60) Provisional application No. 60/128,121, filed on Apr. 7, 1999.

(51) Int. Cl.[7] .................................................. G01N 3/00
(52) U.S. Cl. ...................................................... 73/795
(58) Field of Search ............................ 73/790, 794, 795, 73/798, 789, 94, 818, 788

(56) References Cited

U.S. PATENT DOCUMENTS

| 5,092,179 A | | 3/1992 | Ferguson | 73/790 |
| 5,195,378 A | * | 3/1993 | Ferguson | 73/790 |
| 5,959,215 A | * | 9/1999 | Ono et al. | 73/98 |

FOREIGN PATENT DOCUMENTS

| EP | 0 903 412 | 3/1999 |
| WO | WO 93/08456 | 4/1993 |

OTHER PUBLICATIONS

S. D. Terhune et al, "The Evolution of Microtexture and Grain Boundary Character during ECA Pressing of Pure Aluminum", The Fourth International Conference on Recrystallization and Related Phenomena, Edited by T. Sakai et al, The Japan Institute of Metals, 1999, pp. 515–522.

Horita et al, "Equal–channel Angular pressing for Grain Refinement of Metallic Materials", The Fourth International Conference on Recrystallization and Related Phenomena, Edited by T. Sakai et al, The Japan Institute of Metals, 1999, pp. 301–308.

"Gleeble Systems Application Note—Isothermal Quenching (ISO–Q) Technique for Development of CCT/TTT Diagrams Using Gleeble Systems", Dynamic Systems Inc. application note APN005, 1997, pp. 1–3.

* cited by examiner

Primary Examiner—Benjamin R. Fuller
Assistant Examiner—Octavia Davis
(74) Attorney, Agent, or Firm—Michaelson & Wallace; Peter L. Michaelson

(57) ABSTRACT

Thermodynamic material testing apparatus and a method for use therein which are capable of controllably inducing very large strains in crystalline metallic specimens. The apparatus prevents longitudinal flow elongation, that otherwise results in conventional testing systems when a specimen is compressively deformed, from occurring but permits sideways material flow outwards from a specimen work zone. The specimen is rotated between successive deformations through a predefined angle, e.g., 90 degrees, in order to present strained specimen material to opposing anvil faces for a next successive compressive deformation. Rotating the specimen between hits and hence compressing previously strained material permits the same work zone material to be deformed many times with very high strains induced therein.

21 Claims, 8 Drawing Sheets

APPARATUS FOR A THERMODYNAMIC MATERIAL TESTING SYSTEM THAT PRODUCES VERY LARGE STRAINS IN CRYSTALLINE METALLIC SPECIMENS AND ACCOMPANYING METHODS FOR USE THEREIN

CLAIM TO PRIORITY

This application claims priority of my co-pending United States provisional patent application entitled "Procedure and Apparatus for Making Fine Microstructures in Crystalline Structures", filed on Apr. 7, 1999 and assigned Ser. No. 60/128,121; which is incorporated by reference herein.

BACKGROUND OF THE DISCLOSURE

1. Field of the Invention

The invention relates to apparatus, and an accompanying method for use therein, for a thermodynamic material testing system that is capable of controllably inducing very large strains in metallic structures, specifically in crystalline metallic specimens. Additionally, the system can also simultaneously direct resistance heat or conductively cool such a specimen then under test, under controlled conditions, in order to establish isothermal planes at a desired substantially uniform temperature throughout a work zone in the specimen. The invention is particularly, though not exclusively, suited for simulating the performance of high-speed multi-stand rolling mills and in properly configuring those mills to produce metallic material with very fine-grained crystalline structures.

2. Description of the Prior Art

Metallic materials play an indispensable role as an essential component of an enormous number of different products.

Such materials, with relatively few exceptions, solidify in ordered structures that have atoms arranged in a pattern that repeats itself periodically in three dimensions. Whenever an ordered crystalline structure that forms an entire piece of solid material has a single orientation, the material is viewed as being a single crystal. Polycrystalline aggregates, which are formed of assemblages of large numbers of relatively small crystals, each being a so-called "grain", are the most common form of metals. Within a pure metallic material, each grain has the same composition and structure as that of all of its neighbors, but differs from them in size, shape and orientation. Orientation differences result in the appearance of definite grain boundaries at interfaces between adjacent crystals. These differences significantly affect the properties of the material and to a great extent more so than do the grains themselves.

One important property of a metallic material is its material strength. Commercially speaking, materials with relatively high strengths are extremely. important. A predominant reason is simply that an item can be manufactured to contain less material and hence with generally less weight, if a higher rather than a lower strength material is used. Based on the relative material strength, the weight savings can be appreciable. Oftentimes and not surprisingly, with currently available materials, these weight advantages may well be offset, in certain applications, by increased material cost.

As the grain size of a metallic material decreases, the strength of that material increases. Inclusion of high angle grain boundaries into the material further enhances material strength. Given this, for many decades, considerable effort has been expended in the art to devise and implement techniques for reducing grain sizes, and particularly those techniques that can be used with relatively low cost materials. Clearly, those techniques that readily lend themselves to use in mass production are in greatest demand and hence very eagerly sought by material manufacturers.

Currently, metallic materials are typically fabricated through rolling, forging or extruding-based techniques into sheet, strip or wire, i.e., intermediate products, which are thereafter appropriately and ultimately formed into a shape of a final product. Each of these techniques is governed by interaction of a number of different process parameters all of which significantly influence physical characteristics, such as grain size and shape, and grain boundary orientation, of the final material produced thereby.

Compressively deforming a polycrystalline metal causes its grains to distort. For example, when a metal is rolled, its grains are elongated in a direction of material travel through a rolling mill and cross-wise of longitudinal axes of the rolls, i.e., perpendicular to a roll-metal interface. When a short cylindrical piece of material is compressively deformed, such as through forging, in a direction parallel to a longitudinal cylindrical axis of the material, the length of the cylinder decreases while its diameter increases as the material flows radially outward while it is being deformed; hence, its grains flow elongate here too. Such mechanical working of a metal occurring below its recrystallization temperature, typically referred to as "cold/warm" working, increases internal energy within the crystalline structure. New grains can be formed when additional energy, typically through post-deformation thermal treatment though occurring below the recrystallization temperature, is imparted to the crystalline structure of the material.

The volume of a metallic material at a constant temperature and pressure is itself basically constant. Hence, with the exception of heavily distorted crystalline structures, deforming such a material to change its shape will not appreciably change its volume. When such a material, in the form of a sheet or ingot, is deformed in a rolling mill—i.e., when a roll stand imparts sufficient pressure to the material in excess of the material yield strength, the resulting material will be reduced in thickness but its length will increase. The material will continue to flow elongate as its thickness is increasingly reduced through successive rolling operations.

Grain size and material strength are directly determined through the amount of strain imparted to a metallic material. Deformation causes strain. As the strain increases—up to a point where recrystallization occurs, the microstructure in the material moves, grain refinement occurs and concomitantly grain size decreases. Owing to reduced grain size, the strength of the material increases. Currently, most production rolled steel has a grain size in the 10–50 micron range. If material grain size can be reduced to approximately 1 micron from, e.g., 10 microns, then strength of the resulting material will likely double, if not increase further. Obviously, producing material with such fine grains and high material strengths has profound commercial importance.

In that regard, if lighter materials, such as aluminum, can be processed to yield very small grains and hence significantly enhanced material strengths, then such materials could be used to fabricate parts heretofore formed of heavier materials, such as steel alloys, that possess the same strength. Alternatively, in other applications where material weight may not be an important factor but material cost certainly is, then if relatively low cost materials, such as common low cost steel alloys, could be processed in a fashion that would yield smaller grain sizes and hence increased material strength than heretofore realized in the art, then substantial cost savings will likely result if these materials could replace relatively high-cost high-strength materials.

Another technique commonly used to increase material strength in structural steels has been to alloy various expensive elements into these steels. However, the resulting alloys still tend to be extremely costly and hence economically unsuitable for use in many applications. If the grain size of low-cost steels could be reduced to the point at which such steels possess material strength comparable to that of such alloys, these steels could form a rather cost-effective alternative to such alloys.

Hence, a continual effort has occurred in the art over the course of many years for techniques that can significantly reduce material grain size in order to yield relatively low cost materials that have increased strength.

Mathematically, true strain ($\epsilon$), for a compressive deformation of a specimen, is defined as $-\ln(h_0/h)$ where h is final specimen height and $h_o$ is initial specimen height, and true strain rate is $d\epsilon/dt$ or $-(1/h)(dh/dt)$. Strain is linearly cumulative, provided the specimen material does not recrystallize during an entire deformation process. In that regard, if $\epsilon_i$ represents an amount of strain resulting from deformation i to a specimen, then total strain imparted to that specimen, $\epsilon_t$, is simply a sum of the individuals strains produced by all the deformations (n), as given by equation (1) as follows:

$$\varepsilon_t = \sum_{i=1}^{n} \varepsilon_i \quad (1)$$

Various conventional approaches are taught in the art to reduce grain size. These include, e.g., reduction of metallic material to a very fine powder with subsequent compaction of the powder into a shape of a desired part with or without sintering ("powder metallurgy" based approaches); freezing liquid metallic material by spraying it onto a very cold wheel, typically fabricated of copper, in a fine stream to induce a very high cooling rate; and casting large billets (ingots) or slabs of metallic material which are subsequently reduced to much thinner material by mechanical, i.e., compressive, work to strain the material. Mechanically working such billets or slabs is most commonly used technique where large quantities of material, such as millions of tons of steel or aluminum, need to be formed.

Unfortunately, the capital costs associated with establishing a new production mill, such as a multi-stand rolling mill, for producing a desired intermediate product are staggering in and of themselves. For that reason, relatively few new mills, if any, are currently being built with a marked preference existing in industry to employ appropriate and existing facilities that have requisite idle capacity. However, even with existing facilities, additional sums will often still need to be expended, typically through experimental trials on the mill and using actual material, to properly set the process parameters such that resulting material produced by the mill will possess desired physical characteristics. Given the cost of mill downtime (non-production time), these additional costs can become quite significant in their own right. Hence, a mill owner, seeking as large a return on invested capital as possible, will seek to minimize mill downtime to the extent possible.

Consequently, in an effort to drastically reduce the costs associated with properly setting a production mill or even using it for experimental purposes, considerable effort has occurred in the art, again over the past few decades, and is still occurring, to accurately simulate rolling, forging and extruding techniques, in a laboratory environment, on small metallic specimens. Such simulations, if properly conducted and particularly using proper schedules of material deformation(s) and temperature treatment(s), should yield results that will very accurately, when scaled upward, replicate material behavior under actual production conditions. Fortunately, a rather large number of simulations can be run at an aggregate cost that is typically rather negligible when compared to the cost of even a few hours of lost production from mill downtime; thus, providing a mill owner with an effective experimental avenue for use in determining proper mill settings to yield a desired material but without incurring excessive costs to do so.

While simulations using conventionally available thermodynamic material testing systems, such as the "GLEEBLE" systems manufactured by the present assignee (which also owns the registered trademark "GLEEBLE"), advantageously provide substantial cost and time savings and, for a wide variety of deformation-based processes, yield rather accurate results, these simulations are simply incapable of imparting sufficiently high strain to a specimen that would yield very fine grain sizes.

In particular, currently available material testing systems, such as the "GLEEBLE" systems, can controllably deform a bar specimen along two specimen axes by alternately compressing the specimen at or near its midspan and along axes that are perpendicular to the bar and to each other with a compression being applied along one such axis at a time. If the bar is to remain straight, equal compressive forces are simultaneously applied to opposite sides of the bar. If a small portion of the bar length is compressed near the middle of the bar, typically in a so-called "work zone", as is conventionally done, then, during each compression, specimen material flows from a compressed work zone region towards the ends of the bar causing the bar to elongate. As the bar is alternately compressed along these axes, the volume of material in the work zone will continue to shrink, as the material there is successively compressed, and the bar will continue to elongate. However, such repeated compressions are problematic. In that regard, if a fairly large bar specimen having a square cross-section of 900 mm$^2$ (30 mm-by-30 mm) is compressed along two axes (perpendicular to the major axis of the specimen) to a strain of 4.6, then the resulting bar cross-section will be only 9 mm$^2$ (3 mm-by-3 mm). This cross-section is simply too small to support subsequent test work on the specimen, i.e., successive deformations, as well as machining the specimen to a size needed for further analysis.

Further, even with using lessened amounts of strain, specimen area in the work zone after one or more deformations tends to be relatively small compared to the surface area of the compression face of the anvils. Hence, thermal control of the specimen can be compromised as a result of heat loss occurring through the anvils during each compression. Moreover, while highly uniform micro-structures can be produced using conventional "GLEEBLE" systems, the resulting specimen is often too deformed to be easily held during subsequent machining of its work zone down to a size sufficient for use in subsequent analysis. As such, suitable specimen ends must be added, once all the deformations have been completed, on one axis of the specimen by either welding or bonding to facilitate such machining. Unfortunately, the process used to add these ends often, particularly if it involves welding, corrupts the specimen microstructure produced by the deformations.

Furthermore, if a cylindrical specimen, rather than a bar, were compressively deformed in a longitudinal direction between two compression anvils, then specimen material remaining in the work zone would distort so appreciably when large strains are imparted that the resulting deformed specimen would also no longer be suitable for further deformation or machining. Illustratively, if a strain of 3 is imparted to a specimen having a diameter of 10 mm and a height of 10 mm, the resulting specimen will be compressed to a height of 0.499 mm but with an increased diameter, due to radial flow elongation, of 44.82 mm. Owing to increased surface friction between the material and each anvil, such a large surface area coupled with a thin thickness makes further reductions impractical. Further, the compression anvil would need to have a diameter of at least 50 mm. Consequently, imparting a strain of 10 to such a specimen could not be readily accomplished, if at all. Moreover, should the specimen area perpendicular to an axis of compression exceed a surface area of a compression face of the anvil, then, during any one compression that were to impart a strain over 3, the specimen material, due to flow elongation, would flow beyond the anvil face and hence no longer be compressed. This, in turn, precludes the specimen from being compressed any further; thus, effectively preventing further grain refinement.

Consequently, to yield a specimen that, after being deformed in conventional thermodynamic testing systems, still presents an adequately sized cross-section in view of flow elongation, the total amount of strain that can be induced is typically limited to 2 or less. This amount of strain is simply far less than that needed to cause necessary grain refinement to appreciably reduce the grain size down from a range of 10–50 microns.

The art teaches two other techniques of inducing high strain in a metallic specimen. These techniques involve: (a) rigidly securing each end of a cylindrical bar in a clamp and twisting the bar to introduce torsional deformation to a work-zone, and (b) deforming a cylindrical specimen, by extrusion, through an equal channel angular (ECA) pressing process. However, both of these techniques have proven to be quite problematic in practice and hence rather deficient in accurately simulating production techniques.

Specifically, while a specimen is subjected to torsional deformation, specimen material in the work zone flows in shear planes, with the amount of flow dependent upon an amount of shear. For any point in the work zone, the amount of shear to which material at that point is subjected depends upon a radial distance of that point from an axis about which the specimen ends are twisted, here the longitudinal axis; with torsion being zero along the axis and maximum along a periphery of the specimen. Unfortunately, since the amount of shear is radially dependent, non-uniform deformation results which, in turn, produces non-uniformities in the specimen grain structure; thereby, from a practical standpoint, yielding generally worthless results.

In an ECA pressing process, a billet specimen is pressed, i.e., extruded, under a very high force through a channel that extends longitudinally into a die and has a constant cross-section and a bend. The angle ($\Phi$) of the bend may range from a few degrees of curvature to approximately 90 degrees. For further information on ECA pressing, see, e.g., S. D. Terhune et al, "The Evolution of Microtexture and Grain Boundary Character during ECA Pressing of Pure Aluminum", *The Fourth International Conference on Recrystallization and Related Phenomena, Edited by T. Sakai et al, The Japan Institute of Metals*, 1999, pages 515–522; and Z. Horita et al, "Equal-channel Angular Pressing for Grain Refinement of Metallic Materials", *The Fourth International Conference on Recrystallization and Related Phenomena, Edited by T. Sakai et al, The Japan Institute of Metals*, 1999, pages 301–308. Through the ECA process, the amount of deformation imparted to the specimen obviously increases as the angle of the bend increases to 90 degrees and as a radial distance from an apex (origin) of the arc to a point on the specimen increases. As a result, here, too, the strain imparted to the specimen is highly non-uniform, but with the strain varying across the specimen cross-section. The largest amount of strain, here caused by shear, occurs for the region of the specimen that moves along the largest curvature in the arc, i.e., at the largest radial distance from the apex of the arc. Consequently, to compensate for the non-uniform strain, several pressings are often necessary, with the deformed specimen being rotated typically by 90 degrees between each pressing. Furthermore, owing to the high, but non-uniform strain imparted to the specimen as well as significant friction occurring between the specimen and the channel, the specimen experiences non-uniform heating during each pressing. The heating effects have proven. to be extremely difficult, if at all, to control. Since a crystalline micro-structure is also highly influenced by a temperature, these heating effects further distort the grain structure. Therefore, in view of the very high forces required for this technique and the non-uniform results produced thereby, this technique has proven rather impractical for use in accurately simulating a production environment.

Thus, a need still exists in the art for apparatus for a thermodynamic material testing system, and specifically for such apparatus that can impart, on a practical basis, high strains to a metallic specimen in an amount sufficient to appreciably reduce specimen grain size but in a manner which results in a highly uniform micro-structure, on a cross-sectional basis, throughout the work zone of the specimen. Furthermore, such apparatus should provide accurate control over the temperature of the work zone, by selective and controlled specimen heating and/or cooling, such that a specific schedule of deformation and heat treatments can be imparted to the specimen that collectively and accurately simulate actual warm/cold working production environments. Advantageously, such apparatus could facilitate the development of techniques for massively producing relatively low-cost materials that possess very fine grained micro-structures with significantly increased material strength.

SUMMARY OF THE INVENTION

My invention is capable of imparting high strain uniformly throughout a work zone of such a specimen thus producing a highly uniform, very fine microstructure throughout that zone in a manner that advantageously overcomes the deficiencies associated with conventional material testing systems.

In accordance with my inventive teachings, the inventive apparatus prevents longitudinal flow elongation, that otherwise results in conventional testing systems, when a work zone of a specimen is highly strained, e.g., compressed between two opposing compression anvils, but permits specimen material flow to occur outward, i.e., sideways, from the work zone. Further, the specimen is rotated between successive compressions through an predefined angle, such as 90 degrees, in order to present strained specimen material to the opposing anvil faces for compression during the next hit.

By virtue of this sideways material flow in the work zone, the specimen is simply rotated between successive hits and then the same strained material is compressed again. This process can simply be repeated multiple times, thereby advantageously inducing very high cumulative strains in the work zone. As a result of increasing strain, increasingly fine grain sizes can be produced in the work zone until the cumulative strain causes work zone material to re-crystallize or the work zone to lose its integrity. As such, the amount of strain that can be induced in the work zone is not limited by the apparatus but rather by the work zone material itself.

Such cumulative strains are considerably greater than those obtainable in practice through conventional material testing systems; hence, yielding smaller grain sizes than heretofore possible with those systems.

While the work zone will bulge outward somewhat as a result of each compressive deformation, essentially the same amount of material, with only some slight change, will remain in the work zone after each hit. By repeatedly deforming specimen material that has flowed sideways in the work zone while constraining longitudinal specimen flow elongation, adequately-sized material remains in the work zone itself to readily support subsequent machining and analysis and/or further testing of the specimen. In addition, since the specimen ends themselves, as gripped in the apparatus, do not change size from flow elongation, the resulting specimen can be readily held during such machining without any need to attach separate ends to the specimen. Hence, the inventive technique eliminates any adverse change in the crystalline micro-structure that could otherwise occur through welding or otherwise attaching such ends to the resulting specimen.

Specifically, in accordance with my particular inventive teachings, the specimen work zone is situated between two opposing compression anvils, each of which is movable with respect to the other. The specimen is securely held in a grip assembly in Which the specimen is fixedly restrained between two grips, each of which grips a corresponding end of the specimen, and oriented such that a compression axis of the specimen lies transverse to the longitudinal axis of the specimen. The grip assembly rigidly holds the specimen during each compressive deformation with sufficient force to prevent the specimen from flow elongating as a result of each compression. Furthermore, the grip assembly is mechanically coupled to a torque motor which rotates the grip assembly throughout a predefined partial angular rotation, typically 90 degrees, between successive compressive deformations. As such, the same strained work zone material is successively presented to opposing faces of the compression anvils and then compressed again durin g each such deformation. The velocity at which the anvils move and the distance through which each anvil moves are selectively controlled through a corresponding servo-controlled hydraulic actuator that drives each anvil in order to set a desired strain rate and final strain attainable through each deformation.

In accordance with a feature of my invention, the inventive apparatus also has the capability to pass controlled amounts of alternating (AC) electric current (at power line frequencies) lengthwise through the specimen before, during and/or after each deformation and also, through water quenching internal to the ends of the specimen, to conductively cool the specimen ends from an elevated temperature. This current causes the specimen to self-resistively heat and establish isothermal planes at a desired substantially uniform temperature throughout the work zone of the specimen. By controlling the rates at which the specimen work zone self-resistively heats and then conductively cools, the work zone can be dynamically set to experience any one of a wide range of different time dependent temperature profiles with relatively little, if any, thermal gradients appearing throughout the work zone. Through accurate control of both specimen deformation and work zone temperature, the specimen can undergo not only substantially the same mechanical deformation but also substantially the same thermal processing that will be encountered in a modern medium to high speed multi-stand rolling mill.

Consequently, the inventive apparatus can be used to very accurately simulate such a mill, and in particular to determine proper mill parameters necessary to produce a very fine grained crystalline micro-structure in a metallic material sufficient to impart relatively high strength to that material.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where appropriate, to designate identical elements that are common to the figures.

DETAILED DESCRIPTION

Figure 1:
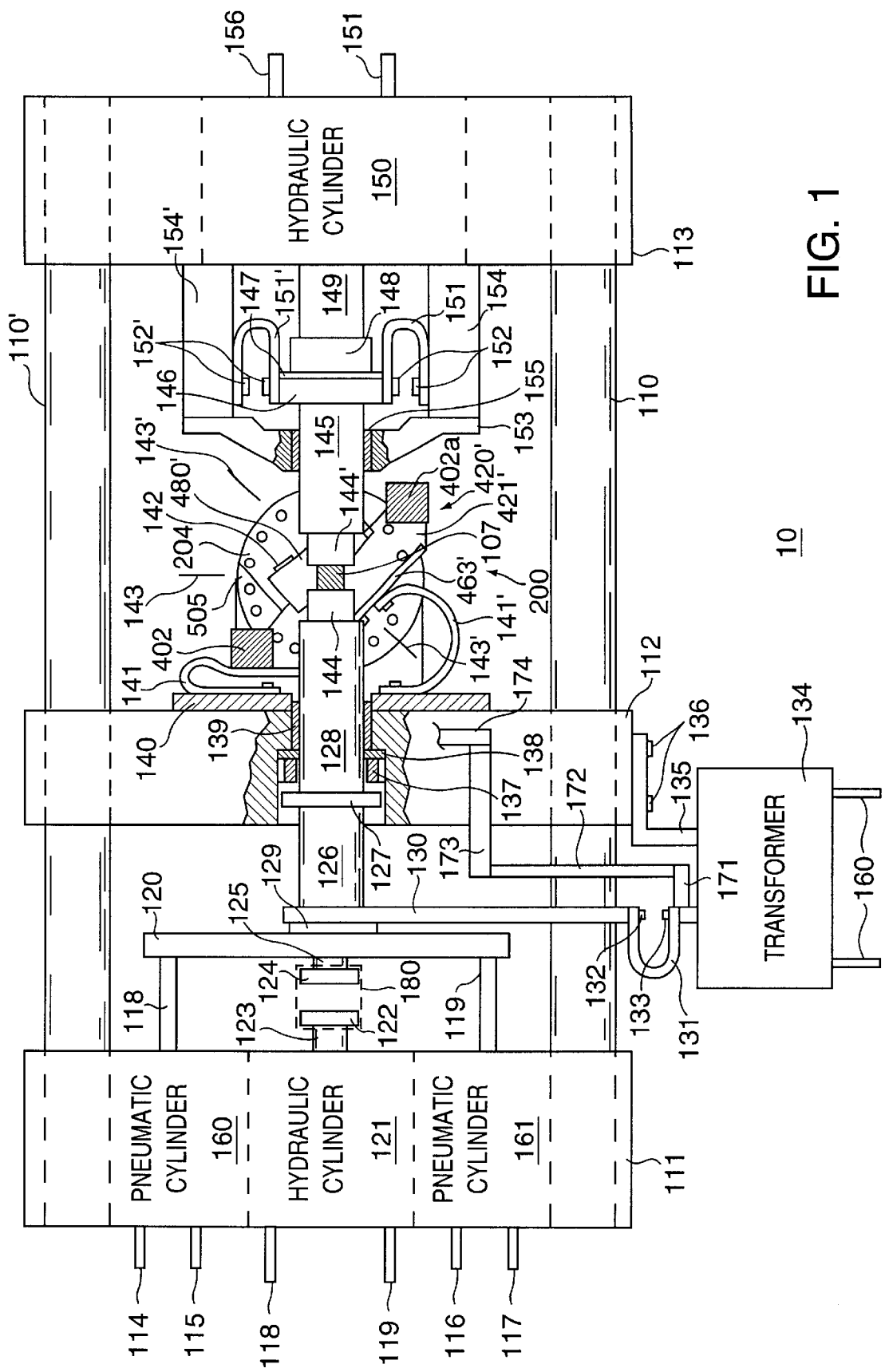
FIG. 1 depicts a schematic diagram, with partial cut-away views, of a preferred embodiment of my inventive apparatus, specifically test stand 10, for imparting high strain to a test specimen as well as a desired thermal profile thereto.

After considering the following description, those skilled in the art will clearly realize that the broad teachings of my invention can be readily utilized in conjunction with any one of a wide variety of material testing systems for simulating a deformation-based production process by successively compressing ("hitting") a test specimen and particularly for highly straining a work zone of that specimen. Through use of the invention, such a testing system, particularly if it can impart a desired thermal profile to the specimen, can accurately simulate deformation and thermal profiles imparted to a metallic material being worked by a modern multi-stand rolling mill. Such a system is well suited for establishing mill parameters needed to produce very fine grains in that material, and hence relatively high strength material. For purposes of illustration and to simplify the following discussion, I will specifically describe my invention in the context of use with illustratively a "GLEEBLE" dynamic thermo-mechanical material testing system of a type currently manufactured by the Dynamic Systems, Inc. (DSI) of Poestenkill, N.Y. (which also owns the registered trademark "GLEEBLE" and is the present assignee hereof).

Advantageously, my inventive apparatus is capable of imparting high strain uniformly throughout a work zone of such a specimen thus producing a highly uniform, very fine microstructure throughout that zone. This is accomplished, in accordance with my inventive teachings, by preventing appreciably, if not totally, all longitudinal flow elongation that otherwise results in conventional testing systems when a specimen is highly strained, e.g., compressed between two opposing compression anvils, but permitting sideways material flow (bulge) outward from the work zone (i.e., in a direction generally transverse to the longitudinal axis of the specimen). Further, in accordance with these teachings, the specimen is rotated between successive compressions through a predefined angle, approximately 90 degrees, in order to present the same strained specimen material to opposing anvil faces for a next compression. Rotating the specimen between successive compressions and hence deforming previously strained material permits the same work zone material to be compressed many times with very high strains induced in the work zone. Hence, increasingly fine grain sizes can be produced until the cumulative strain induced in the work zone causes re-crystallization or loss of work zone integrity. Such cumulative strains, easily exceeding 10, are considerably greater than those obtainable in practice through conventional material testing systems; hence, yielding smaller grain sizes than heretofore possible with those systems.

While the work zone will bulge outward somewhat as a result of each compressive deformation, essentially the same amount of material, with only some slight change, will remain in the work zone after each deformation. Hence, after all the compressions have occurred, the fully deformed specimen will still be adequately sized for later machining for subsequent analysis and/or further testing. Consequently, testing can be started with relatively small specimens, thus providing enhanced thermal control over the specimen work zone while requiring less force to provide each desired deformation. Advantageously, my inventive apparatus can repeatedly compress the specimen as many times as desired, with no effective limit imposed by the apparatus itself.

By repeatedly compressing the same material that has flowed sideways in the work zone while constraining longitudinal specimen flow elongation, adequately-sized material remains in the work zone itself to readily support subsequent machining and analysis and/or further testing of the specimen. In addition, since the specimen ends themselves, as gripped in the apparatus, do not change size from flow elongation, the resulting specimen can be readily held during such machining without any need to attach separate ends to the specimen. Hence, the inventive technique eliminates any adverse change in the crystalline micro-structure that could otherwise occur through welding or otherwise attaching such ends to the resulting specimen.

Specifically, in accordance with my particular inventive teachings, the specimen work zone is situated between two opposing compression anvils, each of which is movable with respect to the other. The specimen is securely held in a grip assembly in which the specimen is fixedly restrained between two grips, each of which grips a corresponding end of the specimen, and oriented such that a compression axis of the specimen lies transverse to the longitudinal axis of the specimen. The grip assembly rigidly holds the specimen during each compressive deformation with sufficient force to prevent the specimen from flow elongating as a result of each compression. Furthermore, the grip assembly is mechanically coupled to a torque motor which rotates the grip assembly throughout a predefined partial angular rotation, typically 90 degrees, between successive compressive deformations ("hits"). As such, the same strained work zone material is successively presented to opposing faces of the compression anvils and then hit again to again compress the same material, hence yielding increasing grain refinement in the work zone. The velocity at which the anvils move and the distance through which each anvil moves during each hit are selectively controlled through a corresponding servo-controlled hydraulic actuator that drives each anvil in order to set a desired strain rate and final strain attainable through each hit.

In sharp contrast, if the specimen were not longitudinally restrained at all—as would occur in conventional material testing systems, then if the work zone were hit in a direction transverse to longitudinal axis of the specimen, the specimen would flow elongate in opposite directions along the latter axis. The specimen would lengthen by a total amount, $\Delta l$, with elongation at each end being $\Delta l/2$. Owing to longitudinal flow elongation occurring during any one deformation, a resulting deformed work zone region would have outwardly sloped walls even if a straight-sided compression anvil were used.

Additionally, the inventive apparatus also has the capability to pass controlled amounts of alternating (AC) electric current (at power line frequencies) lengthwise through the specimen before, during and/or after each "hit" and also, through water quenching internal to the ends of the specimen, to conductively cool the specimen ends from an elevated temperature. This current causes the specimen to self-resistively heat and establish isothermal planes at a desired substantially uniform temperature throughout the work zone of the specimen. By controlling the rates at which the specimen work zone self-resistively heats and then conductively cools, the work zone can be dynamically set to experience any one of a wide range of different time dependent temperature profiles with relatively little, if any, thermal gradients appearing throughout the work zone. Through accurate control of both specimen deformation and work zone temperature, the specimen can undergo not only substantially the same mechanical deformation but also substantially the same thermal processing that will be encountered in a modern medium to high speed multi-stand rolling mill. Consequently, the inventive apparatus can be used to very accurately simulate such a mill, and in particular to determine proper mill parameters necessary to produce a very fine grained crystalline micro-structure in a metallic material and impart relatively high strength to that material.

FIG. 1 depicts a schematic diagram, with partial cut-away views, of a preferred embodiment of my inventive apparatus and specifically test stand 10 for imparting high strain to a test specimen as well as a desired thermal profile thereto. Although this test stand is shown in a horizontal orientation, the stand can be oriented to operate vertically, such as with compressive strokes occurring in a vertical direction, if desired. To simplify the discussion, all references to the drawings will assume a horizontal orientation. Since this apparatus has much in common with the "Hydrawedge" dynamic thermo-mechanical material testing system currently produced by DSI, I will only describe those common elements in sufficient detail necessary to fully understand the present invention. For further details regarding the "Hydrawedge" system, the reader should refer to U.S. Pat. No. 5,092,179 (issued to H. Ferguson on Mar. 3, 1992), which is incorporated by reference herein.

As shown in FIG. 1, test stand 10 contains columns 110 and 110' rigidly mounted within and to cross-heads 111, 112 and 113—all of which form a rigid frame (not specifically referenced), with opposing ends of the columns passing into and being rigidly secured to cross-heads 111 and 113. Both the columns and the cross heads are fabricated from conductive materials. In addition, these components are rigidly constructed to withstand the physical forces occurring during compressive deformation of the specimen. Furthermore, each of these and other components, as discussed below, in test stand 10 has a sufficiently high elastic modulus so as to exhibit relatively little elastic strain during specimen deformation. Test stand 10 also contains hydraulic cylinder 121, and pneumatic cylinders 160 and 161 all mounted within cross-head 111. Air connections 114 and 115, and 116 and 117 are used to operate cylinders 160 and 161, respectively. All these cylinders operate bi-directionally. Air pressure on the order of 1–6 bars (approximately 15 to 90 psi) is applied simultaneously to both pneumatic cylinders.

Piston rods 118 and 119 of pneumatic cylinders 160 and 161 are rigidly attached to cross bar 120. This cross bar is rigidly connected, using non-conductive fasteners, through insulating plate 129 to conductor (power bus) 130 which, in turn, is securely connected to one end of a left shaft assembly containing stub shaft 126, stop plate 127 and compression shaft 128. Each of these fasteners is typically formed of a high strength bolt with an insulated sleeve situated around its shank, an insulated washer at its head and a back-up washer located between the insulated washer and the head.

Stub shaft 126 is secured, at its end opposite conductor 130, to stop plate 127 which, in turn, is attached to one end of anvil shaft 128. The left shaft assembly axially moves within a bore in cross-head 112. Compression anvil 144 is mounted to an opposite end of shaft 128. Stop plate 127 contacts stop ring 137 to prevent further axial movement of the stub shaft and hence limits the stroke of compression anvil 144 and hence the strain produced thereby onto specimen 107. Insulated bolts (not shown) hold the stop ring securely against insulation ring 138 and cross-head 112. Insulated bearing 139 prevents anvil shaft 128 from electrically contacting cross-head 112 and also provides axial guidance for the left shaft assembly. Clearance in the bore prevents the stop plate 127 and the stub shaft 126 from contacting the cross-head.

Anvil 144 compresses one side of the work zone of specimen 107, with the opposite side being compressed by opposing anvil 144'. These anvils are fabricated from materials suitable for deforming the specimens. In the case of hot specimens, such as steel that is to be deformed at 1000° C., each anvil may be formed from tungsten carbide ceramic with a 12% cobalt binder. This anvil material provides high strength at high temperatures. The specimen is held in full restraint between both anvils by rotator assembly 200 (which will be described, including its constituent assemblies, below and in considerable detail in conjunction with FIGS. 2–7). To enhance understanding, assembly 200, depicted in perspective view in FIG. 2 and discussed below, is shown in FIG. 1 in a cross-sectional view taken along lines 1—1 in FIG. 2 in order to expose the anvils and the specimen therebetween.

Returning to FIG. 1, compression anvil 144' is secured to one end of a right shaft assembly, formed of shaft 145, conduction plate 146, insulating plate 147, load cell 148 and cylinder rod 149. Shaft 145 is connected to conduction plate 146, which is connected through insulating plate 147, to load cell 148. The insulating plate electrically insulates the load cell from shaft 145 and plate 146. An end of cylinder rod 149 emanating from hydraulic cylinder 150, which is mounted within cross-head 113, is connected to an end of load cell 148 distal from plate 147. Plate 146 is electrically connected to the frame by rolling flexible conductors (couplings) 151 and 151' which are themselves connected, via fasteners 152 and 152', to through bearing plate supports 154 and 154', respectively. Both of the bearing supports are rigidly and electrically connected at their corresponding ends to cross-head 113. Bearing plate 153, which spans distal ends of these supports. Shaft 145 travels through a bore in plate 153 but is electrically insulated from and axially guided through the bore by insulated bearing 155. As is readily apparent, the left and right shaft assemblies and both compression anvils are all coaxially aligned. The portion of specimen 107 situated between compression anvils 144 and 144' is the work zone.

Power bus 130 is connected, through rolling flexible coupling 131 and bolts 132 and 133, to one output leg of a secondary winding of low voltage, high current transformer 134. This coupling, typically 1.3 cm (approximately 0.5') in total thickness, is formed of a series of parallel copper laminations. Other rolling flexible couplings, as described below, are identically formed. Transformer 134 provides sufficient current flow required to heat metallic specimens of the size employed by test stand 10 and at heating rates equal to or exceeding rates experienced in modern medium to high-speed rolling mills. This current will vary from a few hundred amperes to approximately 22,000 amperes. Though not critical, the transformer should possess a 440 volt, single phase 75 kVA primary with a 5.7 to 10 volt paralleled secondary, preferably controlled by a tap switch, and a 50 or 60 Hz operating frequency. The short circuit output current should be on the order of 50 kA or more. The secondary winding of the transformer is typically formed of one or two turns of a heavy copper casting. By varying the turns ratio of the transformer in finite increments through the tap switch, specimens of different sizes and shapes can be readily heated. Such a transformer is illustratively model G4475NS61S manufactured by Kirkhof Transformer of Grand Rapids, Mich. A return current path for the secondary winding of the transformer is through right angle bracket 135 which is secured, via bolts 136, to cross-head 112. This cross-head is connected to the entire frame of test stand 10. When the anvils are not contacting the specimen, the electrical current path, for self-resistive heating, is, during one half of an AC cycle, from transformer 134, through series-connected copper busses 171, 172, 173 and 174 (buss 174 is only partially shown given the sectioned view of assembly 200 ), all of which are bolted together (through bolts not shown), feed-throughs 366 and 366' (discussed below in conjunction with FIGS. 2 and 3, but not shown in FIG. 1), rolling flexible conductors 320 and 320' and plate 463 (also discussed below in conjunction with FIGS. 2 and 3, and not shown in FIG. 1), to left beam 421 of specimen grip 420 (see FIGS. 2–4 but not shown in FIG. 1), lengthwise through specimen 107 to right beam 421' of specimen grip 420' and, via rolling flexible conductors 141 and 141', plate 140, cross-head 112 and bracket 135, back to transformer 134. Leads 160 are connected to the primary of transformer 134 and carry current thereto from a well-known single current supply (not shown). The current supply is a suitable single phase SCR (silicon controlled rectifier) based thermal control system as is commonly and conventionally used in the GLEEBLE systems.

Piston rod 123 emanating from hydraulic cylinder 121 is connected to coupler 122. Coupler 124 is securely attached, through shaft 125, to cross bar 120. Both couplers have flat faces and are arranged such that these faces are opposing each other. The conventional Hydrawedge system is altered, as shown, by rigidly and tightly connecting couplers 122 and 124 together through high-strength a conventional coupler, represented by dashed box 180, such that piston rod 123 and shaft 125 are mechanically connected together and move in unison. Compression of specimen 107 by compression anvils 144 and 144' begins when piston rods 123 and 149 have sufficiently moved such that compression anvils 144 and 144' engage opposing sides of the specimen work zone. High pressure lines 108 and 109 are connected to inlet and outlet ports of cylinder 121. This cylinder, as well as cylinder 150 connected through hydraulic lines 151 and 156, are controlled by well-known hydraulic servo-control values (not shown) and computer driven control circuits (also not shown) such as those typically found in the GLEEBLE systems manufactured by the present assignee. Both cylinders provide an equal amount of force to equally compress two opposing faces of the work zone of the specimen. Inasmuch as servo-control valves and associated computer control circuits are all very well known in the art, they will not be discussed any further herein. Pneumatic cylinders 160 and 161 provide a much lower force than hydraulic cylinders 121 and 150. In this regard, the combined force of the pneumatic cylinders, at a pressure of 6 bar, may be approximately 1000 pounds (approximately 4380 Newtons) with each hydraulic cylinder providing as much as approximately 20 tons (approximately $8.75 \times 10^4$ Newtons) at a stroke velocity of 2 m/sec.

Test stand 10 can be easily converted for use in a conventional Hydrawedge system by removal of rotator assembly 200, which holds a specimen in longitudinal restraint and is discussed in detail below, and coupler 180. In such a conventional Hydrawedge system, the specimen is rather short and must be supported by the compression anvils at all times. In that case, during operation of that conventional system, pneumatic cylinders 160 and 161 hold the specimen between these anvils by pushing with low force shafts 126 and 128 to the right to squeeze the specimen between the anvils. The force required to overcome drag of pneumatic cylinders 160 and 161 is small compared with the force available from hydraulic cylinder 121. Hence, where test stand 10 is used in accordance with the present invention to impart high strain to a specimen, cylinder 121 is simply controlled to provide necessary additional force to simply overcome this drag. High-strength coupling 180 that mechanically connects shaft 123 to shaft 125 allows cylinder 121 to operate as a normal hydraulic cylinder.

Rotator assembly 200, which holds the specimen in full longitudinal restraint, is mounted to plate 140, which represents an end of a vacuum tank (not shown for clarity and immaterial to the present invention). This plate extends inward and outward from cross-head 112 and is securely bolted to the cross-head. Flexible rolling conductors 141 and 141' connect, through water-cooled copper plate 463', right specimen grip 420' of assembly 200 (which is shown in detail in FIG. 2) to plate 140. Though not completely shown in FIG. 1, the rotator assembly, by virtue of its sectional view taken along lines 1—1 and through a mid-section of this assembly, contains a rigid frame (also referred to herein as a "grip assembly") which holds the specimen in full longitudinal restraint. This assembly is securely fastened, via stiffener plate 204 and using suitable bolts, to a near side of end section 505 of torque motor 500 (see FIG. 2). This frame assembly contains two (left and right) specimen grips 420 and 420', only one of which, specifically right specimen grip 420', is shown in FIG. 1. Yoke struts 402 and 402 a which span the two specimen grips and fixedly secure the specimen grips in place to form the rigid frame are shown in cross-section in this figure, with specimen 107 being shown here as clamped in place in right frame end 421', in specimen grip 420', by clamp 480' using bolts 142. This sectional view omits the near side of the specimen, left specimen grip 420 and its power connections for self-resistively heating the specimen while the anvils are retracted away from the specimen.

Torque motor 500, of which only end member 505 is shown in FIG. 1, is depicted here with the grip assembly in its fully counter-clockwise position. Two additional positions, as indicated by lines 143 and 143' (oriented at 45 and 90 degrees in a clockwise direction, respectively), are provided to permit sufficient angular rotation of the grip assembly such that sideways elongated specimen material resulting from each hit can be presented to the compression anvils for compression during the next hit.

Although FIG. 1 shows compression anvils 144 and 144' in contact with specimen 107, such contact only occurs while the specimen is being deformed. Inasmuch as the specimen is held in place by grip assembly 400, it does not have to be held in position by the anvils. Specimen heating occurs by passing low frequency electrical current lengthwise of the specimen from the specimen grip (e.g., grip 420) on one end of the specimen to the specimen grip (e.g., 420') on the other end of the specimen. Hence, no contact between the anvils and the specimen is needed. Electrical current can also be passed through the anvils and the specimen, or alternatively entirely extinguished during each deformation. Inasmuch as each hit is quite short, typically a few milliseconds in duration, specimen heating will not be adversely affected if heating current is extinguished for such a short period of time. Moreover if the heating current remains on during each deformation, then, while the anvils compress the specimen, the lengthwise current path along the specimen is shorted to the anvils. This may cause locally higher heating at the anvils which can be eliminating by extinguishing the heating current during each hit.

In operation, all the cylinders may be retracted while the specimen 107 is heated. Deformation is done by advancing hydraulic cylinders 121 and 150 at the same speed. Maximum deformation would occur at a point where compression anvils 144 and 144' touch each other. This maximum is never reached since at that point the specimen would be cut in half at its mid span. Deformations on the order of 15% per side are common (for a total deformation of 30%). By keeping the deformation and deformation speed equal, the specimen will not bend during each hit. After a hit occurs, both the compression anvils and all the cylinders are retracted, with the rotator assembly, through suitable control, as described below of torque motor 500, then rotating the rigid frame and specimen 90 degrees in preparation for the next hit. Then, the cylinders are controlled such that the next hit occurs and the work zone is again deformed. The temperature of the specimen can be programmed, by suitable control over the heating current, to change to a desired value or stay the same between successive hits. Such an inter-hit heating schedule permits relatively high specimen heating rates to occur in the work zone. High specimen cooling rates can be obtained where a hole has been previously bored into each end of the specimen to a sufficient depth towards the specimen mid-span and, in the interval between successive hits, circulating cooling water, under pressure, to simultaneously quench the inner-most portion of the wall of each such hole. This modality of cooling such end-bored specimens is provided by the "ISO-Q" (Isothermal Quenching) cooling technique developed by DSI. For further details on this technique, including specimens with reduced end sections, see "Gleeble Systems Application Note—Isothermal Quenching (ISO-Q) Technique for Development of CCT/TTT Diagrams Using Gleeble Systems", Dynamic Systems Inc. application note APN005, 1997, pages 1–3, which is incorporated by reference herein.

Figure 2:
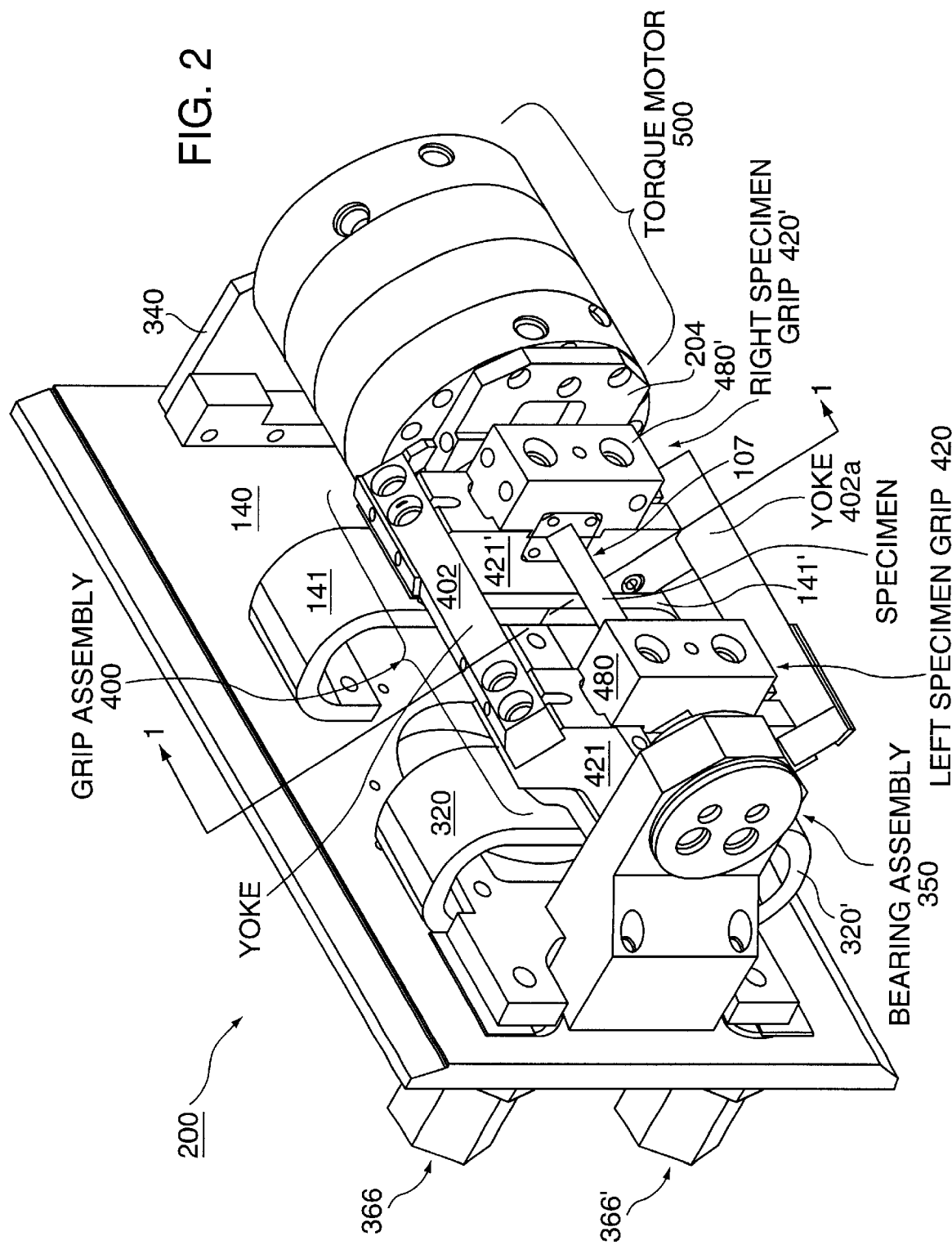
FIG. 2 is a detailed perspective view of rotator assembly 200 that forms part of test stand 10 and incorporates the teachings of my present invention.
Figure 3:
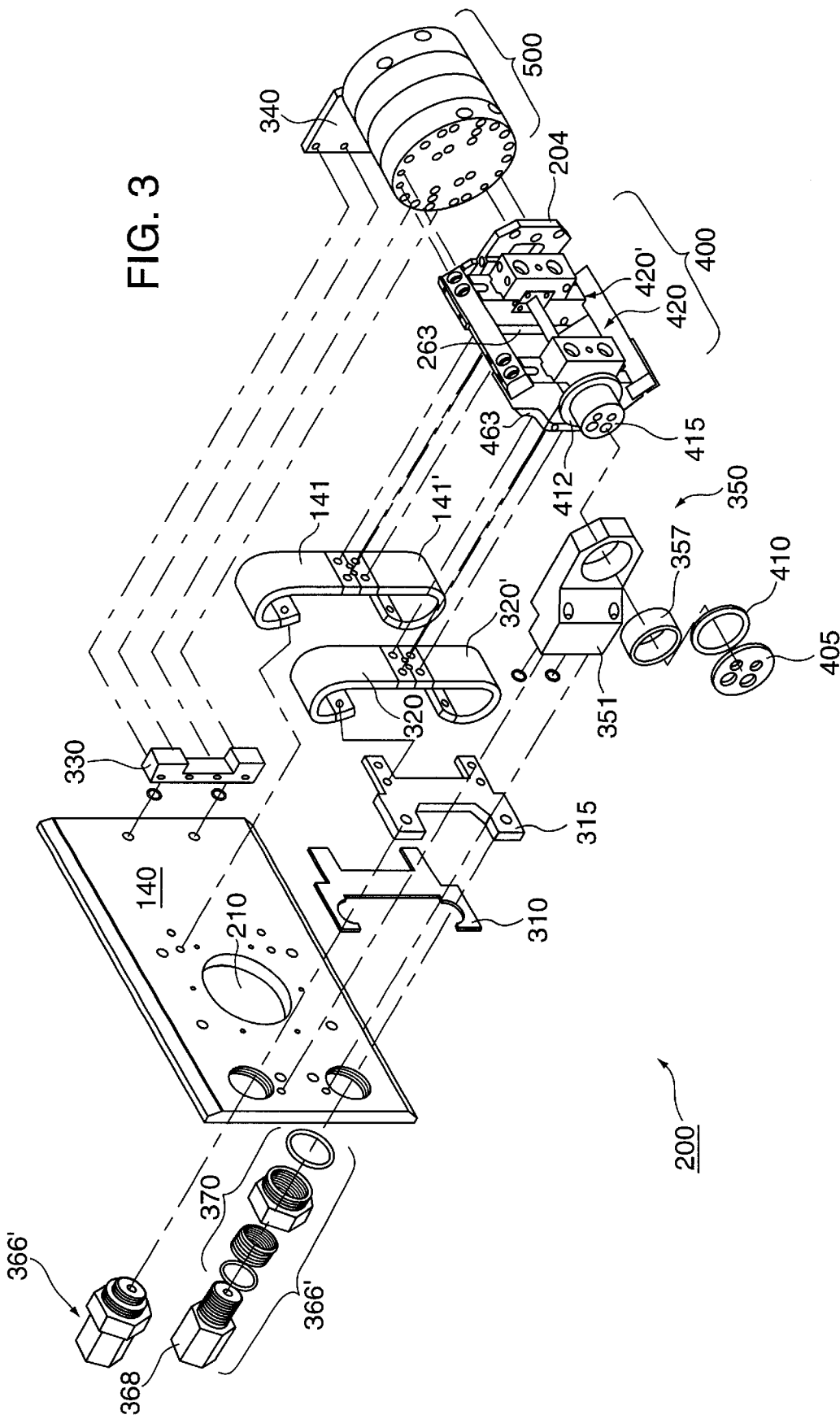
FIG. 3 depicts an exploded view of rotator assembly 200 shown in FIG. 2.

FIG. 2 is a detailed perspective view of rotator assembly 200 as mounted to plate 140, with FIG. 3 being an exploded view of this assembly. To facilitate understanding, the reader should simultaneously refer to FIGS. 2 and 3 throughout the following discussion.

As shown in these two figures, assembly 200 is formed of bearing assembly 350, grip assembly 400 and torque motor 500. Shaft 128 protrudes through hole 210 in this plate (see FIG. 1). As noted above, grip assembly 400 securely holds specimen 107 in full longitudinal restraint, between separate left and right specimen grips, with sufficient force to prevent longitudinal flow elongation during each hit. These separate grips are electrically insulated from each other, carry heating current and are secured together, via yoke struts 402 and 402a, to form a fixed frame. Left and right specimen grips 420 and 420' are formed of left frame end (left beam) 421 and bracket 480, and right frame end (right beam) 421' and bracket 480', respectively. Each frame end and corresponding bracket are bolted together and secure a keyed grip, which is shown in greater detail in FIG. 4, which abuttingly mates with and securely holds a corresponding grooved end of the specimen. Heating current is routed to the left and right specimen grips through roiling flexible conductors 320 and 320', and 141 and 141', which electrically connect, via water cooled copper plates 463 and 263, left specimen grip 420 to plate 315, and right specimen grip 420' to plate 140, respectively. This frame is bolted, via stiffener plate 204, to one side of torque motor 500. The opposite side of the torque motor is securely bolted, via plate 340 and bracket 330, and hence electrically grounded to plate 140.

An opposite side of the frame is mounted to the bearing assembly which, in turn, permits the frame to freely rotate around the longitudinal axis of the specimen as positioned by torque motor 500. Bearing assembly 350 (also shown in FIG. 4) comprises plate 405, mounted to stub shaft 415 and insulator washers 410 and 412 with, as shown in FIG. 3, insulated bearing 357. Referring back to FIGS. 2 and 3, the bearing fits within a bore formed in mounting bracket 351 with the stub shaft slid through the bearing. Washers 410 and 412 are placed on the shaft but on opposite sides of bracket 351. The insulated bearing electrically insulates the end of the rigid frame, specifically the left specimen grip, from mounting bracket 351, thus preventing heating current from being shorted to plate 140, while allowing stub shaft 415 and assembly 400 to freely rotate about the longitudinal axis of the specimen, with the stub shaft itself rotating within the bore in bracket 351. Bracket 351 is mounted directly to plate 140, surrounded by and insulated by space from copper plate 315 and insulating sheet 310, the latter insulating rolling flexible conductors 320 and 320' from plate 140. Distal ends of these rolling flexible conductors are fastened, by bolts, to appropriate points on plate 315. This copper plate is attached to copper feed-through terminals 366 and 366', which protrude through plate 140, to provide a current path for heating current from bus 174 (see FIG. 1; a connection between this bus and the feed-throughs is not explicitly shown in FIGS. 2 and 3 ) to conductors 320 and 320' and hence to the left specimen grip. Copper plate 315 is internally water cooled (not shown). These feed-through terminals, with terminal 366' shown in exploded view, are formed of coupling 368 and assembly 370. Assembly 370 is formed of two fitted insulating bushings, which collectively screw into a corresponding threaded hole in plate 140, sandwiched between two O-ring seals.

Figure 4:
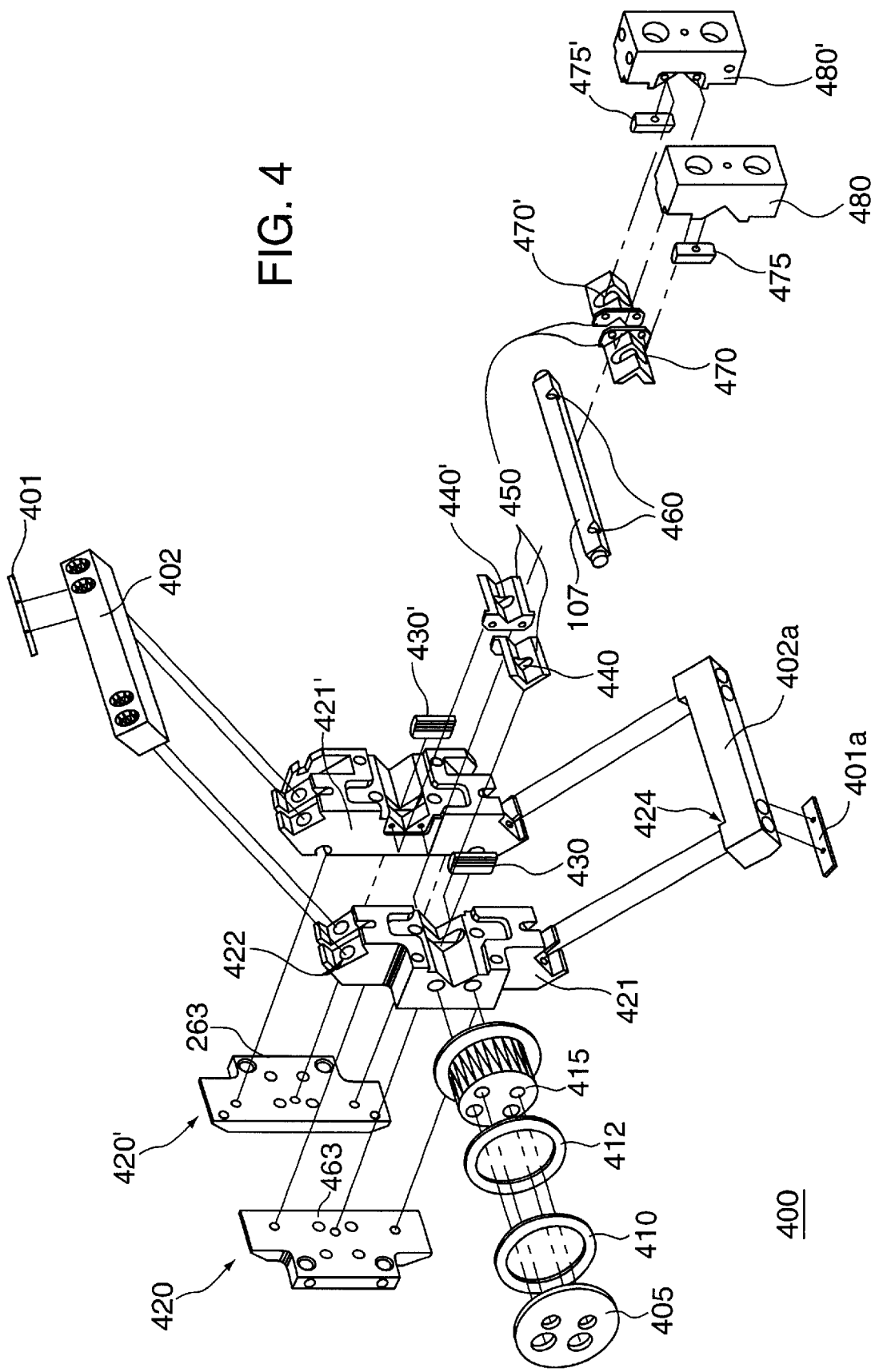
FIG. 4 depicts an exploded view of grip assembly 400 shown in FIGS. 2 and 3.

FIG. 4 depicts an exploded view of grip assembly 400 shown in FIGS. 2 and 3.

As discussed above, a rigid frame is formed of left and right specimen grips (left and right beams) 420 and 420', respectively, securely connected. through yolk struts 402 and 402a. Each strut is fastened to both the left and right beams 421 and 421' using four bolts with insulated bushings and washers (not shown). Additionally, to electrically insulate the struts from the left and right beams and hence prevent heating current from being shunted around the specimen and through the struts, thin insulating plates (not shown) are situated between, inter alia, each contact surface between each strut and the left beam. A step (e.g., step 422 in beam 421 ) in a mounting surface of each beam and an associated step in each end of the strut (e.g., step 424 in strut 402a) collectively provide, when each strut is mounted to the beams and the steps abuttingly mate together, additional rigidity to the frame, thus limiting a potential for the specimen to lengthen the rigid frame when high elongating forces, as a result of each hit, are applied between the specimen grips. If contact surface between the struts and the beams were flat, only the friction provided by tightening insulated bolts that hold the frame together would limit the rigid frame from lengthening during the deformation of the specimen, which may prove, for certain particularly forceful hits, insufficient.

Narrow cushion insulating plates 401 and 401a are fastened to each yoke strut 402 and 402a at corresponding outer corners thereof to prevent the flexible conductors from shorting to the frame assembly when the frame is in either of its two 90 degree positions. In this regard, see FIG. 1 where flexible conductor 401 bends over an upper left corner of yoke strut 402. Insulating plate 401 cushions this conductor around this corner and prevents shorting that would otherwise occur part way up this conductor. The flexible conductor does carry heavy currents, hence a voltage drop occurs across this conductor. Shorting an outer layer of the flexible conductor some distance from its mounting location would disadvantageously cause excessively high local current flow in thin laminated copper web material (0.005 in, approximately 0.125 mm) that forms the conductor. For simplicity of illustration, only two such insulating plates are shown. However, two additional plates (not shown) are fastened to two other corners of these struts from those shown for plates 401 and 401a.

Water cooled plates 463 and 263, which are attached to the rear of beams 421 and 421' and carry electrical current from rolling flexible conductors 320 and 320', and 141 and 141' (the conductors being shown in FIGS. 2 and 3), respectively, are clearly shown.

Furthermore, FIG. 4 clearly shows the manner in which specimen 107 is mounted in longitudinal restraint. This involves keys 430, 430', 475 and 475' which fit into complementary grooves 460 on the specimen after passing through slots 440 and 440', 470 and 470' in insert grips 450. Four grooves are machined into each specimen with two on opposing sides and near each end of the specimen. These grooves collectively accommodate the four keys. When the specimen is clamped securely with the keys in the grooves of the specimen, the specimen is prohibited from lengthening during deformation. Insert grips 450 permit changing the size of the specimen with out changing the clamping system. Once the specimen is assembled to the insert grips with the grooves mated with the keys and the appropriate grips inserted into left and right specimen grips 420 and 420' and brackets 480 and 480', the brackets are rigidly secured to the specimen grips using appropriate bolts.

Figure 5:
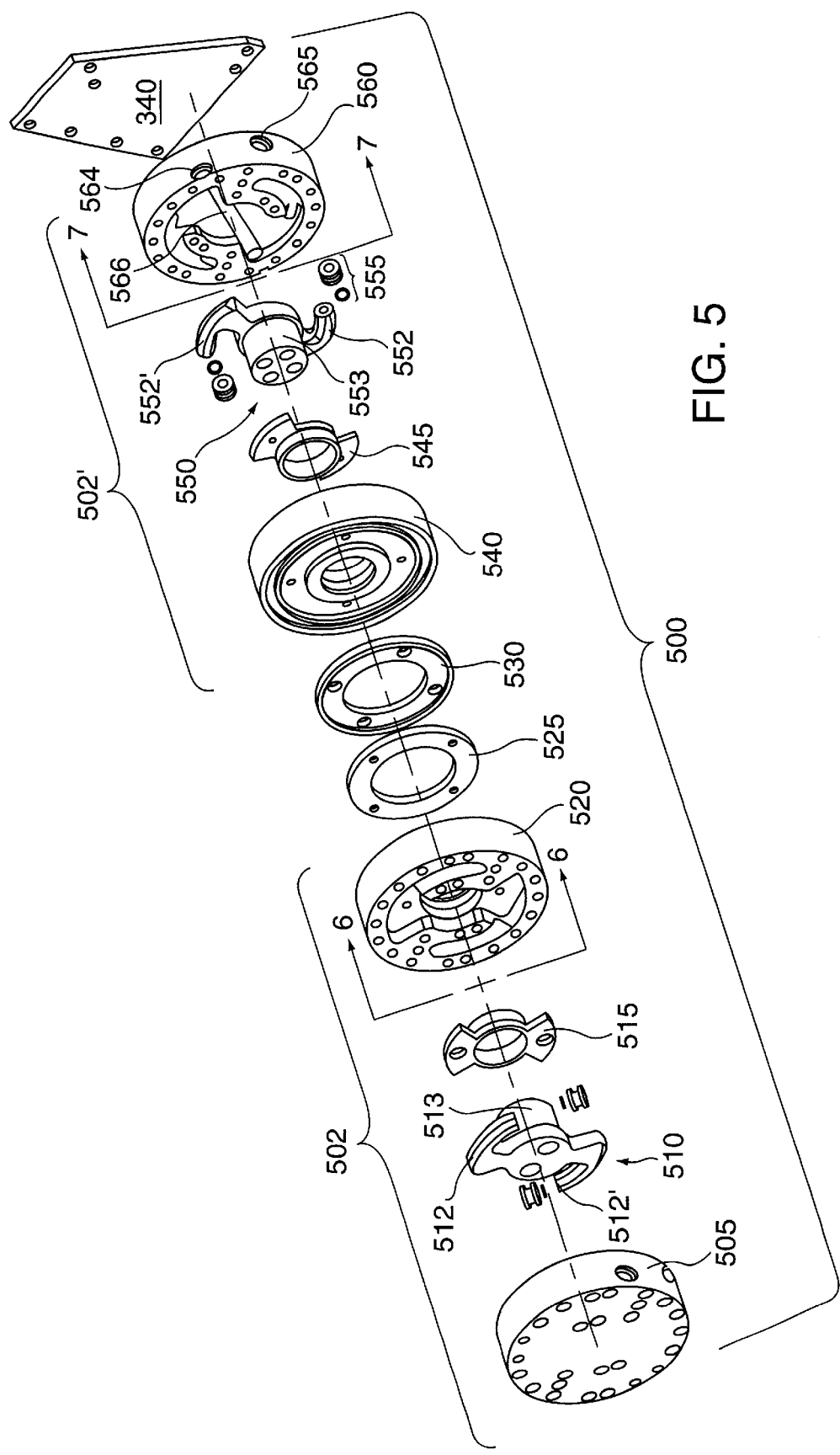
FIG. 5 depicts an exploded in-line view of two-section torque motor 500 that forms a portion of rotator assembly 200 shown in FIGS. 2 and 3.

FIG. 5 depicts an exploded in-line view of torque motor 500 that forms a portion of rotator assembly 200 shown in FIGS. 2 and 3. Front views of motor base 520 and motor end section 560, taken along lines 6—6 and 7—7, are respectively depicted in FIGS. 6 and 7. The rear view of motor end 505 is the same as the front view of motor base 560 shown in FIG. 7, and the rear view of motor base 540 is the same as the front view of motor end section 520 shown in FIG. 6. To facilitate understanding, the reader should simultaneously refer to these three figures throughout the following discussion. As discussed above, one motor end 560, which remains fixed in position, is bolted to plate 340, while face end 505 of the motor is bolted, via stiffener plate 204, to the frame containing the specimen. The motor drives the entire frame, including the yolk struts and the specimen grips, not just the specimen alone. Hence, no external torque is applied to the specimen during its angular rotation. As a result of each such rotation provided by the motor and longitudinal restraint mounting of the specimen, the specimen can be successively compressed on alternate 90 degree flat faces, while the work zone material remains between the compression anvils.

Motor 500 is formed of two identical motor sections 502 and 502'. Each section has dual circumferential pistons that can rotate approximately 45 degrees, thus, with both sections in use, implementing three-position operation; namely, counter-clockwise 45 degrees, center (zero degrees) or clockwise 45 degrees. Total specimen rotation is approximately 90 degrees. In working with specimens having a rectangular (including square) cross-section, there is no need for the motor to stop at any intermediate position, since the specimen will simply be angularly rotated back and forth 90 degrees. The motor is locked in any of these three positions by high hydraulic pressure that exists at that position, typically on the order of 200 bars (approximately 3000 psi). Hence, any potential rotating force resulting from each hit must overcome, at 200 bars, the holding strength provided by the motor, i.e., approximately 680 Newton-meters (N-m) (approximately 6000 in-lbs) of torque, in order to rotate the specimen independent of the mozor.

As detailed in FIG. 5, motor 500 is formed of motor section 502 containing: motor end section 505, rotor 510 having piston arms 512 and 512', bearing 515 and motor base 520; and identical motor section 502' containing: motor base 540, bearing 545, rotor 550, and motor end section 560. Both motor sections abut and slidably rotate against each other through mating bearing/wear plates 525 and 530. The base and end section for each motor section are bolted together (the bolts not specifically shown), but each half is not bolted to the other. High-strength gasket sealant is used to seal the motor base and end sections together thus eliminating leakage of any hydraulic fluid therefrom. Note that if the rotor on either motor section is held, then the housing of that section (base and end section together) will rotate instead, and vice versa. Bearing/wear plate 525 is attached to base 520. Bearing/wear plate 530 is attached to motor base 540. The principal, if not sole, differences between motor sections 502 and 502' are that wear/bearing plates 525 and 530, which separate the two sections, are made, as shown, as a shell and washer, and rotor 510 has a counter bore (not shown) for appropriate bolt heads and rotor 553 has complimentary threads (also not shown) for these bolts which, as noted below, collectively hold these two rotors together. Each of rotors 510 and 550 has two arcuate rotor arms 512 and 512', and 552 and 552', respectively, which form corresponding two circumferential pistons, with suitable piston seals on a distal end of each such piston (of which, e.g., only seals 555 are expressly referenced).

Within motor section 502, arms 512 and 512' are formed on rotor 510 and are spaced radially outward from large diameter shaft 513 which is integral to this rotor, with the arms being oriented in a substantially parallel circumferential direction relative to this shaft. Rotor 553 in motor section 502' is identically formed. When the entire motor is assembled, shaft 513 passes through base 520, bearing/wear plate 525 and abuts against shaft 553 on rotor 550 which passes through base 540 and bearing/wear plate 530 in motor sect on 502'. These two shafts are then bolted and pinned together, with two bolts and two alignment pins, to hold the two motor sections together as well as transfer force therebetween. A small space, typically on the order of 0.2 to 0.3 mm, is provided between the two motor sections.

Figure 6:
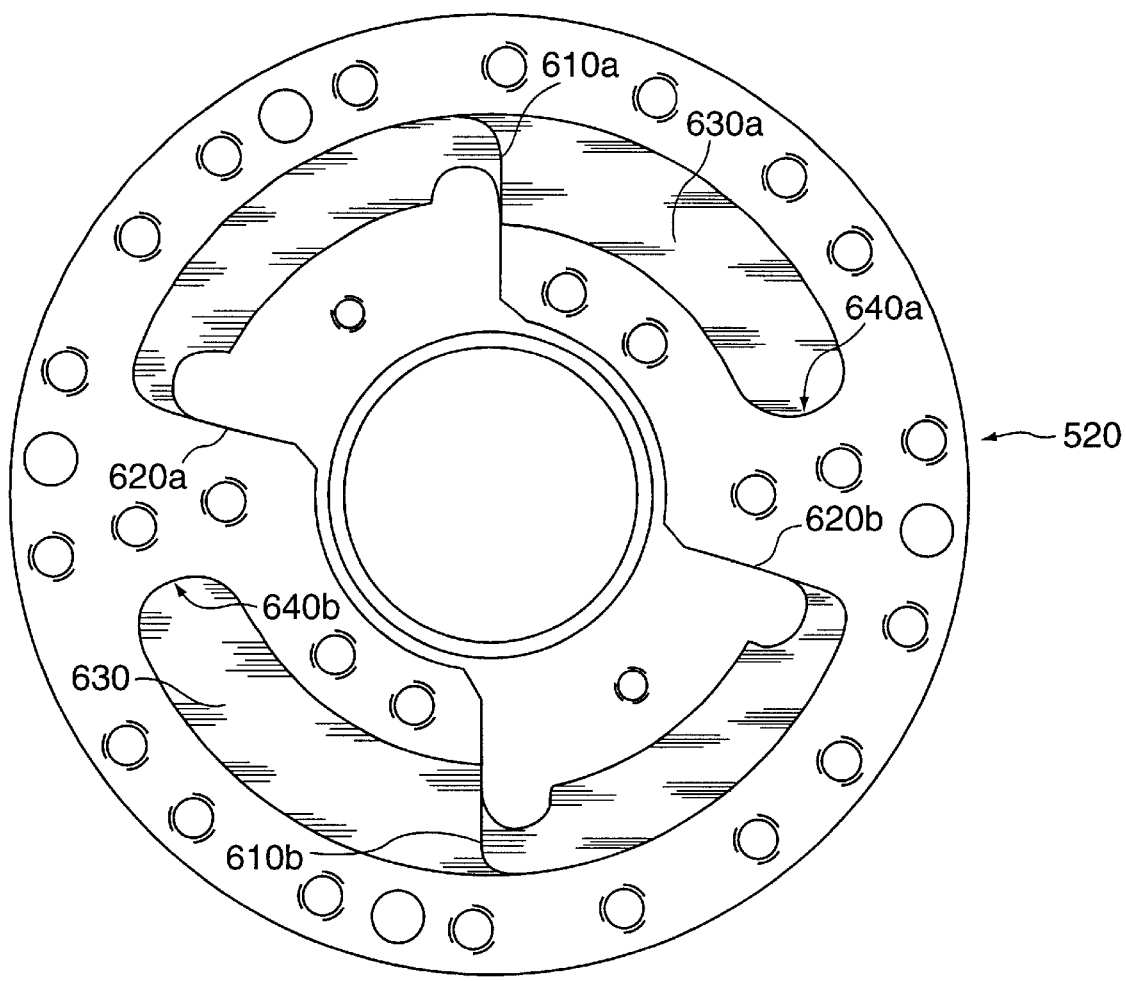
FIG. 6 depicts a front view of motor base section 520, which forms a part of motor 500, shown in FIG. 5 and taken along lines 6—6 therein.
Figure 7:
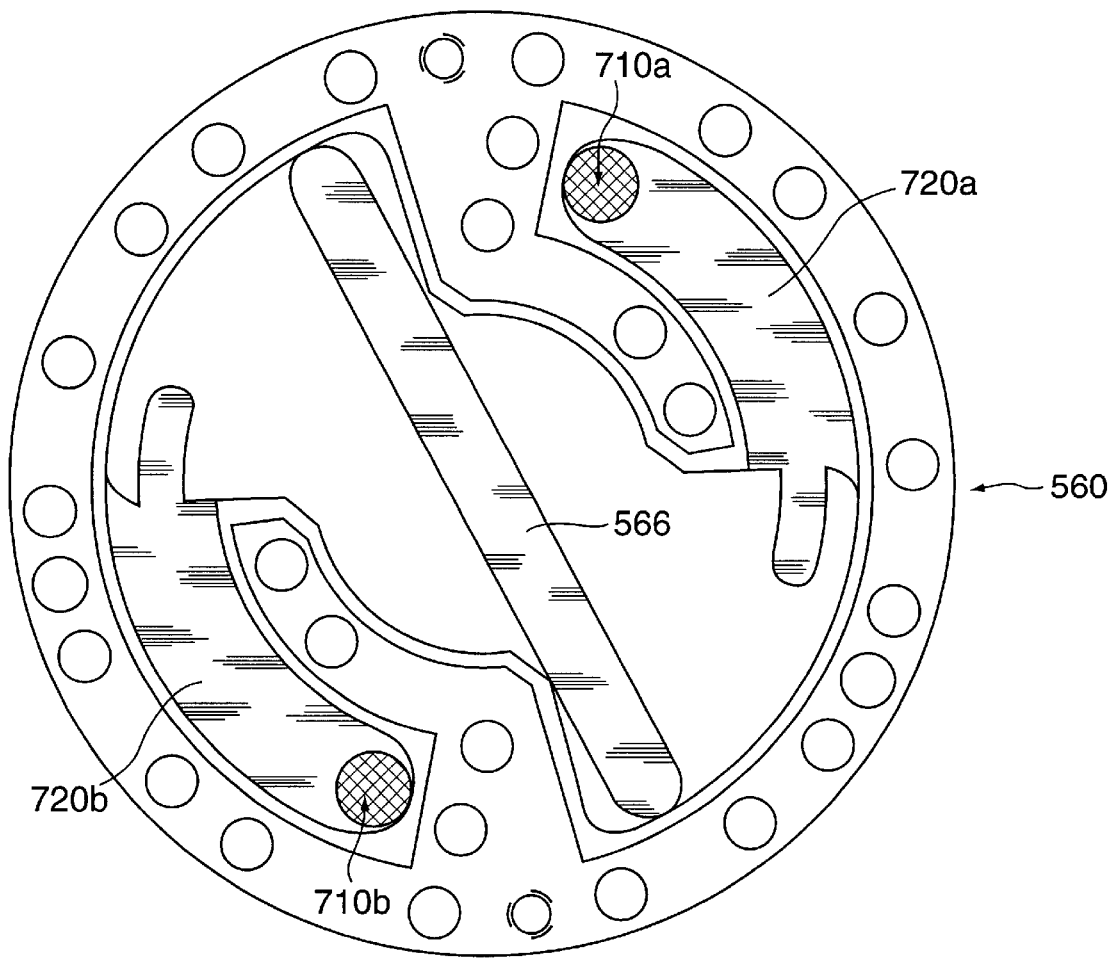
FIG. 7 depicts a front view of motor end section 560, which forms a part of motor 500, shown in FIG. 5 and taken along lines 7—7 therein.

For each rotor, each of its arms nests and moves, under hydraulic pressure, within an arcuate piston cavity complementary to the shape of the arm, with one longitudinal half of the cavity lying in an associated motor base and the other in an associated motor end. As shown in FIGS. 5–7, arms 512 and 512' nest within both cavities 630a and 630b milled in motor base section 520 (identical cavities are milled within motor base 540 to accommodate arms 552 and 552') and opposing mirror-image shaped cavities milled in motor end section 505 (which are identical to cavities 720a and 720b milled in motor end section 560 to accommodate arms 552 and 552'). The two circumferential cylinders in each motor section are effectively formed once the motor base and end section for that half are bolted together, with the rotor situated therebetween. Clearance on the order of approximately 0.1 mm (0.004 inch) is provided between a top of each motor bearing (e.g., bearing 515 mounted in base 520) and an adjacent rotor surface of its rotor (e.g., rotor 510) to minimize free play but assure that the rotors run properly in the circumferential cylinders. The motor base and end sections are bolted tightly together to squeeze gasket sealant located therebetween.

Arms 512 and 512' of rotor 510 are shaped to contact base 520 at locations 620a and 620b, and 610a and 610b at extreme counter-clockwise and clockwise ends, respectively, of their travel. These four locations form positive stops. Motor base 540 for motor section 502' has identical stops.

Preferably, the combined area of the two pistons on each rotor is one square inch (approximately 6.5 cm$^2$) with a radius of its rotor being 2 inches (approximately 5.1 cm). With oil pressure of 200 bar, the resulting torque produced by each motor section is 6000 lb-in (680 N-m) per rotor (3000 pound-inches (340 N-m) per piston). The use of dual pistons per rotor advantageously balances the torque or force on the rotor and bearing assembly.

Pressurized hydraulic oil is routed through two ports on each motor section to move its internal rotor. With respect to motor section 502', port 564 in end section 560 is connected to cavity 566 which extends across the back of rotor 550. Port 565 is connected to a hole (not shown) running under the ends of the cylinders and connected to short holes 710a and 710b. On the one hand, oil pressure applied to port 565 pushes on the distal ends of the pistons formed by arms 552a and 552' forcing clockwise rotation of rotor 550 relative to motor end section 560. Oil pressure applied to port 564, on the other hand, applies pressure on the opposite proximal ends of the rotor arms and hence the back side of the pistons forcing counter clockwise rotation of the rotor 550 relative to motor end section 560. While, as previously noted, oil pressure on the order of 200 bars can be used, suitable operation can be effected with oil pressure of only 60 bars. Identical hydraulic ports and cylinder operation occurs in motor section 502.

Hence, as noted, during operation, the housing, of motor section 502', formed of motor base 540 and end section 560, is rigidly mounted to plate 340, thus preventing their rotation, while the housing of the other motor section, 502, formed of motor end section 505 and base section 520, is free to rotate with the frame. In particular, when both cylinders in motor section 502' are suitably pressurized through port 565, rotor 550 causes its shaft and that of rotor 510 to rotate 45 degrees. Consequently, since these two rotors rotate together, the housing for motor section 502 then rotates by 45 degrees. Then, energizing rotor 510, through separately pressurizing the dual cylinders in this particular motor section, causes further rotation of its own housing by another 45 degrees; hence rotating the frame (and its restrained specimen) attached to end section 505 by a total of 90 degrees. There is appreciably no high-speed undershoot or overshoot in these positions when inter-pass time becomes critical.

Alternately, rather than using a ganged two-section torque motor as described above, two separate torque motors can be used with each one attached using a suitable keyed clamp to a corresponding end of the specimen. However, this alternate approach requires that the bearings on the torque motors be able to handle very high axial loads in order to prevent the specimen from flow elongating. Since an extension force (resulting from flow elongation) of a specimen being deformed can easily exceed 20 tons, these separate torque motors would require extremely heavy thrust bearings. The rigid frame, as discussed above and shown in FIGS. 2–4, which separately supports the specimen and restrains the elongation force, advantageously absorbs the large elongating force instead of the torque motor, thus advantageously eliminating any need for such thrust bearings.

Regardless of the approach taken, i.e., use of a rigid frame or two separate torque motors, the ends of the specimen must be effectively restrained during each deformation (hit) such that resulting material flow is sideways from the work zone and not by any appreciable (preferably no) longitudinal elongation. Such sideways flow allows the specimen to simply be rotated with the deformed, i.e., strained, work zone material hit again and further deformed, and this process repeated many times, such that very high strains can be imparted to the work zone material, hence advantageously yielding very fine crystalline micro-structures therein.

Figure 8:
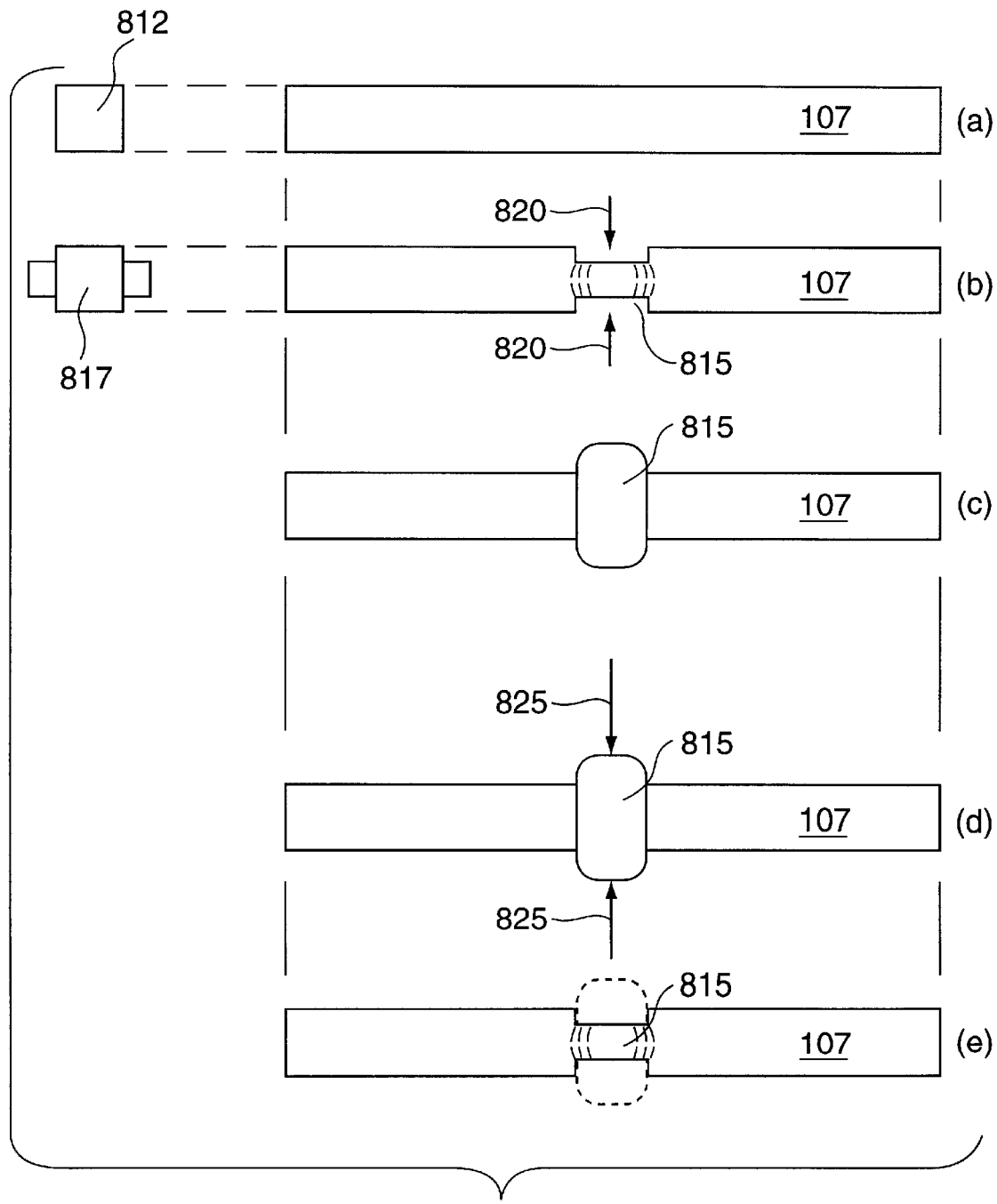
FIG. 8 depicts, through side views (a)–(e) and cross-sectional views 812 and 817, a multi-hit compressive deformation sequence for imparting high strain to a work zone of illustrative test specimen 107 by inventive test stand 10.

FIG. 8 depicts a multi-hit compressive deformation sequence for imparting high strain to a work zone of illustrative test specimen 107 by inventive test stand 10. Initially, specimen 107, before any hits, appears as in side view (a) with square cross-section 812. Thereafter, the work zone is deformed (compressed) in directions shown by arrows 820 in side view (b). As a result of the specimen being fully longitudinally restrained, specimen material in work zone 815 flows sideways outward from the work zone, hence producing specimen cross-section 817. The specimen is then rotated 90 degrees through movement of the torque motor, as previously described, to present the strained work zone material, that has flowed sideways, to the compression anvils. At this point, the specimen appears as in side view (c) with specimen material in work zone 815 bulging outward. Thereafter, the strained work zone material is hit by the compression anvils along directions shown by arrows 825, as shown in side view (d), resulting in side view (e). In the latter side view, specimen material in work zone 815 has again been compressed as indicated by dashed lines and has flowed sideways (bulged outward) once again. The steps of rotating the specimen 90 degrees and deforming the same work zone material, previously deformed, can be repeated many times in order to accumulate strain in this material to any desired level, prior to this material recrystallizing or simply losing integrity.

While I have described the actuators that drive both compression anvils as servo-controlled hydraulic cylinders, clearly these actuators can be any one of a wide variety of other force producing devices, such as, e.g., screw jacks, that can generate requisite force, stroke length and stroke rate.

Furthermore, though, for simplicity, the preferred embodiment of the inventive testing apparatus utilizes a specimen with a square cross-section and imparts a single hit at a time to two opposing work zone faces, this embodiment could be modified to utilize specimens with differently shaped cross-sections, e.g., having an even number of faces in excess of four, such as hexagonal, octagonal, etc., with different corresponding angular rotations between hits to present work zone material that has just been strained to the compression anvils for a subsequent hit. Moreover, multiple hits could occur simultaneously, where each hit is applied to two opposing work zone surfaces. Depending on the compressive force applied to the specimen and amount of deformation achieved, multiple simultaneous hits might accumulate strain faster than if a square-shaped specimen were to be used and thus lessen a number of rotation-hit cycles needed to accumulate a desired amount of strain. However, the resulting apparatus capable of performing multiple simultaneous hits would likely be quite complex and costly.

Although a single preferred embodiment which incorporates the teachings of my present invention has been shown and described in considerable detail herein, those skilled in the art can readily devise many other varied embodiments that still incorporate these teachings.

I claim:

1. A material testing system, which is capable of imparting high strain test specimen, comprising:

a deforming device for controllably and successively deforming a work zone of the specimen in a direction transverse to a longitudinal axis of the specimen so as to define a deformation direction and to produce successive deformations in the specimen, by compressing the specimen between a pair of opposing surfaces of the work zone, and impart cumulative strain to the work zone;

a grip assembly for securely holding the specimen at both of two longitudinal ends thereof with sufficient rigidity during each of said deformations such that the specimen, as a result of compressive force imparted by the deforming device to the specimen during said each deformation, does-not experience appreciably any flow elongation along the longitudinal axis, and material flow in the work zone of, the specimen, resulting from each said deformation, substantially occurs outward from the work zone and in a direction transverse to the longitudinal axis and away from the deformation direction, thus producing strained work zone material; and a device for rotating the specimen through a predefined angle after each of the deformations has occurred so as to expose a next successive pair of opposing surfaces of the work zone to the deforming device and, by so doing, present the strained work zone material to the deforming device such that the strained work zone material is deformed again during a next successive one of the deformations;

whereby strain is increasingly accumulated in the work zone through repeated deformations between successively changing opposing surfaces of the strained work zone material while volume of the strained work zone specimen material remains essentially constant throughout all the deformations, thus imparting said high strain to the specimen.

2. A method for use in a material testing system for imparting high strain to a test specimen, the method comprising the steps of:

(a) controllably deforming a work zone of the specimen in a direction transverse to a longitudinal axis of the specimen so as to define a deformation direction and to produce a deformation in the specimen, by compressing the specimen between a pair of opposing surfaces of the work zone, and impart strain to the work zone;

(b) securely holding the specimen at both of two longitudinal ends thereof with sufficient rigidity during said deformation such that the specimen, as a result of compressive force imparted by the deforming step to the specimen during the deformation, does not experience appreciably any longitudinal flow elongation along the longitudinal axis, and material flow in the work zone of the specimen resulting from the deformation substantially occurs outward from the work zone and in a direction transverse to the longitudinal axis and away from the deformation direction, thus producing strained work zone material;

(c) rotating the specimen through a predefined angle after the deformation has occurred so as to expose a next successive pair of opposing surfaces of the work zone to the deforming device and, by so doing, present the strained work zone material to the deforming device such that the strained work zone material is deformed again during a next successive deformation; and (d) repeating steps (a)–(c) in order to accumulate increasing amounts of strain in the work zone through repeated deformations between successively changing opposing surfaces of the strained work zone material while volume of the strained work zone material remains essentially constant throughout all the deformations, thus imparting said high strain to the specimen.

3. The system recited in claim 1 wherein the deforming device comprises at least one anvil for imparting a compressive deformation to the work zone.

4. The system recited in claim 3 wherein the deforming device further comprises first and second anvils, wherein the first and second anvils apply equal compressive forces to opposing sides of the work zone to produce each of the deformations.

5. The system recited in claim 4 further comprising first and second servo-controlled actuators for controllably driving the first and second anvils, respectively, each with a predefined stroke distance and stroke rate, in order to impart a desired amount of strain to the work zone during each of the deformations.

6. The system recited in claim 5 wherein each of the first and second actuators comprises either an hydraulic cylinder or a screw jack.

7. The system recited in claim 4 wherein the grip assembly comprises:

first and second specimen grips which securely grip first and second longitudinal ends of the specimen so as to hold the specimen on a lengthwise basis; and first and second struts affixed to and bridging the first and second specimen grips, which, in conjunction with the first and second specimen grips, form a frame which restrains the specimen from experiencing said longitudinal flow elongation during each of said deformations.

8. The system recited in claim 7 wherein each of the first and second specimen grips comprise at least one key which engages with a corresponding groove on a surface of the specimen so as to further prevent longitudinal flow elongation of the specimen.

9. The system recited in claim 7 further comprising a torque motor attached to the frame for rotating the frame, while the frame holds the specimen, through the predefined angle.

10. The system recited in claim 9 wherein the predefined angle is approximately 90 degrees.

11. The system recited in claim 9 wherein the torque motor comprises:

first and second motor sections rotatable with respect to each other, said first and second motor sections having first and second housings and first and second rotors, respectively; and wherein:

the first housing is coupled to the frame and the second housing is coupled to a fixed portion of the apparatus; and the first and second rotors are coupled together for common rotation within and relative to the housings of, the first and second motor sections, respectively.

12. The system recited in claim 11 wherein each of the first and second rotors has dual circumferential arms extending therefrom, with each of said arms being moveable within a complementary arcuate-shaped piston cavity formed within a corresponding one of the first or second housings, thereby forming dual circumferential pistons.

13. The system recited in claim 7 further comprising a current supply for controllably providing current lengthwise through the specimen in order to self-resistively heat the work zone.

14. The system recited in claim 13 wherein the current supply is controlled to apply the current to the specimen between successive ones of the deformations.

15. The system recited in claim 14 further comprising electrical conductors for routing the current between the current supply and through the first and second specimen grips such that the current flows lengthwise through the specimen.

16. The method of claim 2 further comprising the step of imparting a compressive deformation to the work zone through at least one anvil.

17. The method of claim 16 wherein the deforming step further comprises the step of applying equal compressive forces to opposing sides of the work zone, through first and second anvils, to produce each of the deformations.

18. The method of claim 17 further comprising the step of rotating a frame, while the frame holds the specimen, through the predefined angle through a torque motor attached to the frame.

19. The method of claim 18 wherein the predefined angle is approximately 90 degrees.

20. The method of claim 17 further comprising the step of controllably providing current lengthwise through the specimen in order to self-resistively heat the work zone.

21. The method of claim 20 wherein the current providing step comprises the step of applying the current to the specimen between successive ones of the deformations.

* * * * *